US008450281B2

(12) United States Patent
Bernardi et al.

(10) Patent No.: US 8,450,281 B2
(45) Date of Patent: May 28, 2013

(54) NON-IMMUNOSUPPRESSIVE CYCLOSPORIN FOR TREATMENT OF ULLRICH CONGENITAL MUSCULAR DYSTROPHY (75) Inventors: Paolo Bernardi, Padua (IT); Gregoire Vuagniaux, Lausanne (CH); Rafael Crabbe, Bursins (CH)

(73) Assignee: Debiopharm S.A., Lausanne (CH)

( * ) Notice: Subject to any disclaimer, the term of this patent is extended or adjusted under 35 U.S.C. 154(b) by 467 days.

(21) Appl. No.: 12/522,118

(22) PCT Filed: Jan. 3, 2008

(86) PCT No.: PCT/IB2008/000003
§ 371 (c)(1),
(2), (4) Date: Aug. 14, 2009

(87) PCT Pub. No.: WO2008/084368
PCT Pub. Date: Jul. 17, 2008

(65) Prior Publication Data
US 2010/0041593 A1    Feb. 18, 2010

Related U.S. Application Data (60) Provisional application No. 60/878,414, filed on Jan. 4, 2007.

(51) Int. Cl.
*A61K 38/13* (2006.01)
*A61K 38/00* (2006.01)
(52) U.S. Cl.
USPC .......................................... 514/20.5; 514/1.1
(58) Field of Classification Search
None
See application file for complete search history.

(56) References Cited

U.S. PATENT DOCUMENTS

| | | | |
|---|---|---|---|
| 6,268,398 B1 * | 7/2001 | Ghosh et al. | 514/634 |
| 6,280,981 B1 * | 8/2001 | Dykens et al. | 435/110 |
| 6,927,208 B1 * | 8/2005 | Wenger et al. | 514/3.8 |
| 2010/0323972 A1 * | 12/2010 | Molkentin | 514/20.5 |

FOREIGN PATENT DOCUMENTS

| | | |
|---|---|---|
| WO | WO 03/049682 A2 | 6/2003 |
| WO | WO 2005/021028 A1 | 3/2005 |

OTHER PUBLICATIONS

Angelin et al. Mitochondrial dysfunction in the pathogenesis of Ullrich congenital muscular dystrophy and prospective therapy with cyclosporins. PNAS, Jan. 10, 2007, vol. 104, No. 3, pp. 991-996.*
Lampe et al. Collagen VI related muscle disorders. Review. J Med Genet. 2005. vol. 42, pp. 673-685.*
Bonaldo et al. Collagen VI deficiency induces early onset myopathy in the mouse: an animal model for Bethlem myopathy. Human Molecular Genetics, 1998, vol. 7, Nol. 13, pp. 2135-2140.*
Irwin, WA, et al, Nat Ganet, Dec. 2003; 35(4): 367-71. Epub Nov. 16, 2003. Abstract Only; "Mitochondrial dysfunction and apoptosis in myopathic mice with collagen VI deficiency".
Lampe, AK, et al, J Med Genet, Sep. 2005; 42(9); 673-85 Abstract Only; "Collagen VI related muscle disorders."
Hansson, M.J., et al, *Journal of Bioenergetics and Biomembranes*, vol. 36, No. 4, Aug. 2004, pp. 407-413, "The Nonimmunosuppressive Cyclosporin Analogs NIM811 and UNIL025 Display Nanomolar Potencies on Permeability Transition in Brain-Derived Mitochondria".
Irwin, W.A., et al, *Nature Genetics*, vol. 35, No. 4, Dec. 2003, pp. 367-371, "Mitochondrial dysfunction and apoptosis in myopathic mice with collagen VI deficiency".
Office Action dated Nov. 20, 2012 issued in connection with Japanese Patent Appln. No. 2009-544475—Japanese language.
Office Action dated Nov. 20, 2012 issued in connection with Japanese Patent Appln. No. 2009-544475—English Translation.
Bernardi et al, "The mitochondrial permeability transition from in vitro artifact to disease target", FEBS Journal 273:2077-2099 (2006).

* cited by examiner

*Primary Examiner* — Marcela M Cordero Garcia
(74) *Attorney, Agent, or Firm* — Nixon & Vanderhye P.C.

(57) ABSTRACT

The present invention relates to the use of a nonimmunosuppressive cyclosporin A derivative for reducing mitochondrial dysfunction and the rate of apoptosis of muscle cells of patients diagnosed with Ullrich congenital muscular dystrophy or Bethlem myopathy.

3 Claims, 5 Drawing Sheets

NON-IMMUNOSUPPRESSIVE CYCLOSPORIN FOR TREATMENT OF ULLRICH CONGENITAL MUSCULAR DYSTROPHY

This application is the U.S. national phase of International Application No. PCT/IB2008/000003, filed 3 Jan. 2008, which designated the U.S. and claims priority to U.S. Application No. 60/878,414, filed 4 Jan. 2007, the entire contents of each of which are hereby incorporated by reference.

FIELD OF THE INVENTION

The present invention relates to the use of a nonimmunosuppressive cyclosporin A derivative for reducing mitochondrial dysfunction and the rate of apoptosis of muscle cells of patients diagnosed with Ullrich congenital muscular dystrophy or Bethlem myopathy.

BACKGROUND OF THE INVENTION

Inherited mutations of collagen VI genes cause two main skeletal muscle diseases, Bethlem myopathy (BM, Online Mendelian Inheritance in Man [OMIM] 158810), and Ullrich congenital muscular dystrophy (UCMD, OMIM 254090).

BM is an autosomal dominant disorder characterized by slowly progressive axial and proximal muscle weakness with flexion finger contracture. (Bethlem and Wijngaarden. Brain 1976; 99: 91-100; Merlini et al. Neuromuscul Disord 1994; 4: 503-11). It presents intrafamiliar variability and different clinical onset from prenatal to mid-adulthood. Prenatal onset is characterized by decreased fetal movements; neonatal onset by hypotonia or torticollis; early-childhood onset by delayed motor milestones, muscle weakness and contractures; and adult onset by proximal weakness, achilles tendon and fingers contractures. The condition is usually mild and slowly progressive with some affected individuals over 50 years of age needing aids for outdoors mobility. (Pepe et al. Biochem Biophys Res Commun 1999; 258: 802-07. De Visser et al. Muscle Nerve 1992; 15: 591-96). Cardiac function is usually normal.

UCMD is an autosomal recessive disorder characterized by congenital muscle weakness with joint contractures and coexisting distal joint hyperlaxity. (Ullrich. Z. Ges. Neurol. Psychiatr. 1930; 126: 171-201. Camacho Vanegas et al. Proc Natl Acad Sci USA 2001; 98: 7516-21.) The presentation is usually at birth with hypotonia, congenital hip dislocation, prominent calcanei, and a transient kyphotic deformity. Motor milestones are delayed and most of the children never acquire the ability to walk independently. Follicular hyperkeratosis over the extensor surfaces of upper and lower limbs and keloid and cigarette paper scar formation are common. Axial muscle involvement is severe resulting in progressive scoliosis with spine rigidity. Early and severe respiratory involvement may require artificial ventilatory support in the first or second decade of life. The subjects affected by UCMD have a normal intelligence, and MRI shows a normal brain development. Patients with recessive or de novo heterozygous mutations usually have a classic severe phenotype, although they may occasionally present a milder Bethlem-type disease. (Pan et al. Am J Hum Genet. 2003; 73: 355-69. Baker et al. Hum Mol Genet. 2005; 14: 279-93. Demir et al. Am J Hum Genet. 2002; 70: 1446-58.) In some patients with the UCMD phenotype, mutations of collagen VI genes were excluded, suggesting genetic heterogeneity even for this condition. (Pan et al. Am J Hum Genet. 2003; 73: 355-69).

Recently, it was shown that mice lacking collagen VI due to targeted inactivation of the Col6a1 gene have a latent mitochondrial defect caused by inappropriate opening of the permeability transition pore (PTP), an inner membrane channel that plays a role in several forms of cell death and can be desensitized by cyclosporin A. (Irwin et al. Nat Genet. 2003; 35: 267-71. Bernardi et al. FEBS J 2006; 273: 2077-99.) This finding was further exploited in vivo, and led to successful therapeutic intervention in the mouse model. Establishing whether mitochondria are involved in the pathogenesis of the genetically and clinically heterogeneous UCMD represented a major challenge, which was the main hurdle to the therapeutic application in humans of the regimen defined in the mouse model. This challenge has now been overcome. Furthermore, the present inventors have been able to demonstrate that latent mitochondrial defects present in cells of UCMD patients and resulting elevated rates of apoptosis can be inhibited by non-immunosuppressive cyclosporin A derivatives such as $[\text{D-MeAla}]^3\text{-}[\text{EtVal}]^4\text{-CsA}$. Consequently, the present invention provides for a new method for inhibiting apoptosis of muscle cells of patients suffering from UCMD and a new method of treatment of this disease in these patients using a non-immunosuppressive derivative of cylosporin A, preferably $[\text{D-MeAla}]^3\text{-}[\text{EtVal}]^4\text{-CsA}$. No effective method for treating UCMD is presently available. Hence, there is a need for new therapeutic approaches such as that described herein. The present inventors were also able to uncover a similar mitochondrial defect in BM patients that was sensitive to cyclosporin A. Hence, the new method of treatment disclosed herein for UCMD patients is also applicable for the treatment of BM patients.

SUMMARY OF THE INVENTION

The present invention derives from the finding that a key problem in UCMD is an elevated rate of apoptosis of cells of skeletal muscles. This elevated rate could be shown by the inventors to be a result of a latent mitochondrial dysfunction that could be corrected by exposure of the cells to cyclosporin A. Importantly, non-immunosuppressive cyclosporin A derivative $[\text{D-MeAla}]^3\text{-}[\text{EtVal}]^4\text{-CsA}$ was as effective in reducing mitochondrial dysfunction and suppressing excessive apoptosis as the parent compound. Therefore, the present invention relates to the use of a non-immunosuppressive cyclosporin A (CsA) derivative of formula I, more preferably a nonimmunosuppressive cyclosporin A derivative of formula II and most preferably nonimmunosuppressive cyclosporin A derivative $[\text{D-MeAla}]^3\text{-}[\text{EtVal}]^4\text{-CsA}$ of formula II, for reducing mitochondrial dysfunction and apoptotic rates in cells of patients suffering from UCMD. Non-immunosuppressive cyclosporin A derivatives suitable for use with the present invention were described in International Patent Application PCT/EP2004/009804 by Novartis AG (WO2005/021028), on pages 3-6. $[\text{D-MeAla}]^3\text{-}[\text{EtVal}]^4\text{-CsA}$ was disclosed in U.S. Pat. No. 6,927,208.

Formula I wherein
W is MeBmt, dihydro-MeBmt, 8'-hydroxy-MeBmt or O-acetyl-MeBmt,
X is αAbu, Val, Thr, Nva or O-methyl threonine (MeOThr), R is Pro, Sar, (D)-MeSer, (D)-MeAla, or (D)-MeSer (Oacetyl),
Y is MeLeu, thioMeLeu, γ-hydroxy-MeLeu, MeIle, MeVal, MeThr, MeAla, MeaIle or MeaThr; N-ethylVal (EtVal), N-ethylIle, N-ethylThr, N-ethylPhe, N-ethylTyr or N-ethylThr(Oacetyl), wherein Y cannot be MeLeu when R is Sar,
Z is Val, Leu, MeVal or MeLeu,
Q is MeLeu, γ-hydroxy-MeLeu, MeAla or Pro,
$T_1$ is (D)Ala or Lys,
$T_2$ is MeLeu or γ-hydroxy-MeLeu, and
$T_3$ is MeLeu or MeAla.

Formula II wherein
W' is MeBmt, dihydro-MeBmt, or 8'-hydroxy-MeBmt,
X is αAbu, Val, Thr, Nva or O-methyl threonine (MeOThr),
R' is Sar, (D)-MeSer, (D)-MeAla, or (D)-MeSer(Oacetyl),
Y' is MeLeu, γ-hydroxy-MeLeu, MeIle, MeVal, MeThr, MeAla, MeaIle or MeaThr; N-ethylVal (EtVal), N-ethylIle, N-ethylThr, N-ethylPhe, N-ethylTyr or N-ethylThr(Oacetyl), wherein Y cannot be MeLeu when R is Sar,
Z is Val, Leu, MeVal or MeLeu,
Q' is MeLeu, γ-hydroxy-MeLeu, or MeAla.

Moreover, the invention relates to pharmaceutical compositions for the treatment of UCMD comprising an effective amount of a nonimmunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula II, a pharmaceutically acceptable carrier and, optionally, an excipient and a diluent. The diluent typically is water. Excipients that are typically added to parenteral formulations include an isotonic agent, a buffer or other pH-controlling agent, and a preservative. The compositions may comprise other active ingredients such as an antibiotic.

The present invention further relates to the use of a nonimmunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III, for reducing mitochondrial dysfunction and apoptotic rates in cells of patients suffering from Bethlem myopathy. Moreover, the invention also concerns a method for treatment of BM in a patient comprising administering to the patient an effective amount of a non-immunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III. Further, the invention also relates to use of a nonimmunosuppressive Formula III wherein MeBmt is N-methyl-(4R)-4-but-2E-en-1-yl-4-methyl-(L)threonine, αAbu is L-α-aminobutyric acid, D-MeAla is N-methyl-D-alanine, EtVal is N-ethyl-L-valine, Val is L-valine, MeLeu is N-methyl-L-leucine, Ala is L-alanine, (D)Ala is D-alanine, and MeVal is N-methyl-L-valine.

In another embodiment, the invention relates to the use of a nonimmunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III, for the manufacture of a medicament intended for the treatment of UCMD.

In a further embodiment, the invention concerns a method for treatment of UCMD in a patient comprising administering to the patient an effective amount of a non-immunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III. An effective amount of a nonimmunosuppressive cyclosporin A derivative is understood to be an amount that when administered repeatedly in the course of a therapeutic regimen to a UCMD patient results in an objective clinical response such as an improvement, stabilization or slow-down in the progression of the disease. When administered orally, an effective amount for daily or trice weekly administration will be between about 1 mg/kg to about 100 mg/kg, preferably from about 1 mg/kg to about 20 mg/kg. By the intravenous route, the indicated corresponding dosage may be from about 1 mg/kg to about 50 mg/kg, preferably from about 1 mg/kg to about 25 mg/kg.

cyclosporin A derivative of formula I, II or III for the manufacture of a medicament intended for the treatment of BM. Finally, the invention relates to pharmaceutical compositions for the treatment of BM comprising an effective amount of a non-immunosuppressive cyclosporin A derivative of formula I, II or III, a pharmaceutically acceptable carrier and, optionally, an excipient and a diluent.

BRIEF DESCRIPTION OF FIGURES

[EtVal]$^4$-CsA to the incubation medium. Panel A: each point represents a single mouse. Mice 24-27 were treated with [D-MeAla]$^3$-[EtVal]$^4$-CsA, and mice 28-31 with a placebo formulation.

DETAILED DESCRIPTION OF THE INVENTION

To assess whether an increased incidence of apoptosis and a latent mitochondrial dysfunction could be revealed in UCMD patients, five patients affected by UCMD were studied in reference to healthy individuals. Patients 1 and 5 had genetically proven UCMD. (Demir et al. Mutations in COL6A3 cause severe and mild phenotypes of Ullrich congenital muscular dystrophy. *Am J Hum Genet.* 2002; 70: 1446-58. Giusti et al. Dominant and recessive COL6A1 mutations in Ullrich scleroatonic muscular dystrophy. *Ann Neurol* 2005; 58: 400-10.) In patient 2, sequence analysis of COL6A1 exon 9 revealed the presence of a 15 nucleotidest deletion (spanning nucleotidest 35.374-35.388 of accession number AJ011932, corresponding to a genomic clone including exons 1-20 of COL6A1 gene; nt 921-936 of accession number NM_001848, corresponding to COL6A1 transcript) occurring in heterozygosity. In patient 4, sequence analysis of COL6A1 exon 9 revealed the presence of a G→A variation occurring in heterozygosity (nucleotide 35.400 of accession number AJ011932; nucleotide 850 of accession number NM_001848). Genetic analysis was not available for patient 3, who presented the typical clinical and immunohistochemical features of UCMD.

The five patients were representative of the spectrum of severity of UCMD: all had a congenital onset; three (patients 2, 3 and 5) never achieved the ability to stand and walk; one (patient 4) was only able to stand with support; and one (patient 1) achieved the ability to walk. The decrease of collagen VI ranged from mild (patients 1 and 4), to marked (patients 2 and 3), to complete absence (patient 5). The mutation affected the COL6A1 gene in three cases (patients 2, 4 and 5), the COL6A3 gene in one case (patient 1) and was undefined in one case (patient 3).

Biopsies from a quadriceps muscle of the five patients and a healthy volunteer were obtained subsequent to patient informed consent and ethics committee approval. The rate of apoptosis was assessed using the terminal deoxynucleotidyl transferase-mediated dUTP nick end labelling (TUNEL) method. Seven-μm-thick frozen sections were prepared from muscle biopsies and fixed in 50% acetone-50% methanol. TUNEL was performed using the Apoptag in situ apoposis detection kit (Chemicon). Samples were stained with peroxidase-diaminobenzidine to reveal TUNEL-positive nuclei and counterstained with Hoechst 33258 (Sigma) to label all nuclei. The number of total and TUNEL-positive nuclei was determined in randomly selected fields using a Zeiss Axioplan microscope (40× magnification) equipped with digital camera. Data were expressed as mean±S.D. Data were analyzed with the unpaired Student's t-test, and values with P<0.01 were considered as significant. Results revealed that the frequency of apoptotic nuclei was much higher in all the patient samples when compared to the healthy donor, with values ranging from an approximately 10-fold increase for patients 1, 2 and 3 to a more than 200-fold increase for patients 4 and 5. Increased apoptosis corresponded with a significantly decreased expression of collagen VI in the muscle biopsies from all patients, as documented by staining with a selective antibody against collagen VI.

Experiments were carried out to experimentally test the existence of a causal link between lack of collagen VI and apoptosis. Myoblast cultures were prepared from muscle biopsies of two unaffected controls and from patients 1, 2, 3 and 4 by enzymatic and mechanical treatment and plating in Dulbecco's modified Eagle's medium (DMEM) supplemented with 20% fetal calf serum, penicillin, streptomycin and amphotericin B (Sigma). To test for apoptosis, cells were fixed in 50% acetone-50% methanol and processed for TUNEL analysis using the Dead End Fluorescence TUNEL System (Promega). Visualization of all nuclei was performed by staining with Hoechst 33258. Cultures from all patients displayed a higher incidence of apoptosis compared to healthy donors. Plating on collagen VI or treatment with cyclosporin A fully normalized the occurrence of apoptosis in the patient samples. Muscle cell cultures from patients 2, 3 and 4 expectedly displayed low to nearly absent levels of collagen VI, as had already been shown previously for patients 1 and 5. Demir et al. 2002. Giusti et al. 2005.

To assess whether the anti-apoptotic effects of collagen VI and CsA could be traced to mitochondria, mitochondrial function was studied in living muscle cell cultures. As expected, addition of oligomycin to cultures established from the healthy donors did not cause mitochondrial depolarization, which was promptly elicited by the addition of the protonophore carbonylcyanide-p-trifluoromethoxyphenyl hydrazone. Addition of oligomycin was instead followed by mitochondrial depolarization in the cells from all UCMD patients. Remarkably, the response to oligomycin was fully normalized by treatment with cyclosporin A or intracellular $Ca^{2+}$ chelator BAPTA-AM, or by plating cells on collagen VI, suggesting an involvement of the PTP in the pathogenesis of UCMD. Mitochondrial membrane potential was assessed based on accumulation of tetramethylrhodamine methyl ester (TMRM). It is noted that oligomycin was expected to cause hyperpolarization in healthy, respiring cells in which the mitochondrial membrane potential is maintained by proton pumping by the respiratory chain and the proton electrochemical gradient is used to drive ATP synthesis. The mitochondrial depolarization induced by oligomycin in UCMD myoblast cultures was, therefore, an anomalous response, which indicated that the membrane potential was not maintained by respiration but rather by the mitochondrial ATP synthase working "in reverse" to pump protons from the matrix to the intermembrane space, thereby consuming glycolytic ATP.

The muscle cell cultures established from healthy donors and from patients 1, 2 and 3 were studied by electron microscopy. In the UCMD samples, the mitochondrial area/perimeter ratio was significantly increased to attain values 62.5, 75 and 50% higher than those of healthy donors for patient 1, 2 and 3, respectively (p<0.05). This finding indicates that in UCMD muscle cells, mitochondria were significantly less elongated than in normal samples. It was also observed that 4 to 8% of mitochondria of patients had an increased short axis value (>400 nm) compared to the control (<300 nm). Taken together, these findings suggested the presence of a fraction of mitochondria with increased size in UCMD cells. A small percentage of cells from UCMD patients (between 4 and 5%, as compared to 1% for cells from healthy donors) also displayed swollen mitochondria, with hypodense matrix and absence of cristae. Remarkably, when the UCMD cells had been plated on collagen VI, the area/perimeter ratio and short axis values became similar to those of healthy donors; and plating on collagen VI or treatment with cyclosporin A decreased the number of cells with swollen mitochondria to the values observed in cultures from healthy donors.

Treatment of cultures with the F1FO ATP synthase inhibitor oligomycin increased the percentage of cells with swollen mitochondria to 4% in control and to over 40% in UCMD patients, a finding suggesting the presence of a latent mitochondrial dysfunction that could be selectively amplified by oligomycin, as previously shown for the mouse model of collagen VI deficiency. The effect of oligomycin could be prevented by treatment with cyclosporin A, the percentage of cells bearing swollen mitochondria being restored to values similar to basal in all cell cultures. Non-immunosuppressive cyclosporin A derivative [D-MeAla]$^3$-[EtVal]$^4$-CsA was as effective as cyclosporin A in preventing oligomycin-dependent mitochondrial depolarization in cells from UCMD patients and restored the occurrence of apoptosis to the level displayed by cells from healthy donors. The experiments that resulted in these findings are discussed under Example 1.

It is remarkable that the mitochondrial defect can be revealed in primary cultures from patients with clinical signs of UCMD irrespective of whether the primary genetic defect is in the COL6A1 or COL6A3 gene and that the latent mitochondrial abnormality is not predictive of the severity of the clinical syndrome. These findings suggest that mitochondria are involved in the pathogenesis of all cases of UCMD, and that additional genetic and/or environmental factors play a role in the individual susceptibility to muscle fiber demise and regeneration. All mitochondrial abnormalities and the ensuing apoptosis could be cured by plating UCMD cells on collagen VI or exposing them to cyclosporin A. These findings demonstrate that, in principle, the pathogenic chain of events downstream of the genetic lesion can be interrupted by appropriate drugs, at least at the early stages. Cyclosporin A is well known to cause immunosuppression, which could be a major drawback in long-term treatment of patients. A key observation made by the present inventors is that non-immunosuppressive cyclosporin A derivative [D-MeAla]$^3$-[EtVal]$^4$-CsA is as effective as cyclosporin A in reducing mitochondrial dysfunction and apoptotic rates in UCMD cells. This finding demonstrates that the immunosuppressive activity of cyclosporin is not involved in its cytoprotective effects and provides for a new pharmacological treatment of patients affected by collagen VI disorders.

Based on these findings, the present invention relates to the use of a non-immunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III, for reducing mitochondrial dysfunction and apoptotic rates in cells of patients suffering from UCMD.

Formula I wherein
W is MeBmt, dihydro-MeBmt, 8'-hydroxy-MeBmt or O-actetyl-MeBmt,
X is αAbu, Val, Thr, Nva or O-methyl threonine (MeOThr),
R is Pro, Sar, (D)-MeSer, (D)-MeAla, or (D)-MeSer (Oacetyl),
Y is MeLeu, thioMeLeu, γ-hydroxy-MeLeu, MeIle, MeVal, MeThr, MeAla, MeaIle or MeaThr; N-ethylVal (EtVal), N-ethylIle, N-ethylThr, N-ethylPhe, N-ethylTyr or N-ethylThr(Oacetyl), wherein Y cannot be MeLeu when R is Sar,
Z is Val, Leu, MeVal or MeLeu,
Q is MeLeu, γ-hydroxy-MeLeu, MeAla or Pro,
T$_1$ is (D)Ala or Lys,
T$_2$ is MeLeu or γ-hydroxy-MeLeu, and
T$_3$ is MeLeu or MeAla.

Formula II wherein
W' is MeBmt, dihydro-MeBmt, or 8'-hydroxy-MeBmt,
X is αAbu, Val, Thr, Nva or O-methyl threonine (MeOThr),
R' is Sar, (D)-MeSer, (D)-MeAla, or (D)-MeSer(Oacetyl),
Y' is MeLeu, γ-hydroxy-MeLeu, MeIle, MeVal, MeThr, MeAla, MeaIle or MeaThr; N-ethylVal (EtVal), N-ethylIle, N-ethylThr, N-ethylPhe, N-ethylTyr or N-ethylThr(Oacetyl), wherein Y cannot be MeLeu when R is Sar,
Z is Val, Leu, MeVal or MeLeu,
Q' is MeLeu, γ-hydroxy-MeLeu, or MeAla.

Formula III wherein MeBmt is N-methyl-(4R)-4-but-2E-en-1-yl-4-methyl-(L)threonine, αAbu is L-α-aminobutyric acid, D-MeAla is N-methyl-D-alinine, EtVal is N-ethyl-L-valine, Val is L-valine, MeLeu is N-methyl-L-leucine, Ala is L-alanine, (D)Ala is D-alanine, and MeVal is N-methyl-L-valine.

A nonimmunosuppressive cyclosporin A derivative can be used to inhibit apoptosis in vitro in muscle-derived cells prepared from biopsies taken from UCMD patients. A finding of inhibition of apoptosis will serve as an indicator that treatment of the patients with the nonimmunosuppressive cyclosporin A derivative will be effective in reducing the severity of the disease.

The invention also relates to the use of a nonimmunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III, for treating patients suffering from UCMD. The active compound, i.e., the nonimmunosuppressive cyclosporin A derivative, may be administered by any conventional route. It may be administered parentally, e.g., in the form of injectable solutions or suspensions, or in the form of injectable deposit formulations. Preferably, it will be administered orally in the form of solutions or suspensions for drinking, tablets or capsules. Pharmaceutical compositions for oral administration comprising nonimmunosuppressive cyclosporin A derivative [D-MeAla]$^3$-[EtVal]$^4$-CsA are described in Examples. As is demonstrated by the examples, such pharmaceutical compositions typically comprise the non-immunosuppressive cyclosporin A derivative of choice and one or more pharmaceutically acceptable carrier substances. Suitable pharmaceutical carriers are described, e.g., in Remington's Pharmaceutical Sciences, 17$^{th}$ ed., Mack Publishing Company, Easton, Pa. (1990), which is a standard reference text in this field. Sometimes these compositions are concentrated and need to be combined with an appropriate diluent, e.g., water, prior to administration. Pharmaceutical compositions for parenteral administration typically also include one or more excipients. Optional excipients include an isotonic agent, a buffer or other pH-controlling agent, and a preservative. These excipients may be added for maintenance of the composition and for the attainment of preferred ranges of pH (about 6.5-7.5) and osmolarity (about 300 mos m/L).

Additional examples of cyclosporin formulations for oral administration can be found in U.S. Pat. Nos. 5,525,590 and 5,639,724, and U.S. Pat. Appl. 2003/0104992. By the oral route, the indicated dosage of non-immunosuppressive cyclosporin A derivative for daily to trice weekly administration may be from about 1 mg/kg to about 100 mg/kg, preferably from about 1 mg/kg to about 20 mg/kg. By the intravenous route, the indicated corresponding dosage may be from about 1 mg/kg to about 50 mg/kg, preferably from about 1 mg/kg to about 25 mg/kg. An effective amount of non-immunosuppressive cyclosporin A derivative is understood to be an amount that when administered repeatedly in the course of a therapeutic regimen to a UCMD patient results in an objective clinical response such as an improvement, stabilization or slow-down in the progression of the disease. Such clinical response can be assessed, e.g., by Quantitative Isometric Strength (QIS) testing. QIS allows evaluation of muscle strength in an objective way with the aid of pressure transducing and recording equipment. Alternatively, normalization of rates of apoptosis can be assessed in muscle biopsies by biochemical and immunohistochemical methods known to the person skilled in the art. Finally, electromyography may be utilized that shows a muscular instead of a neurogenic pattern, which may be quantified.

Initial phase I clinical studies were carried out to assess the safety of oral doses of [D-MeAla]$^3$-[EtVal]$^4$-CsA, and to determine the pharmacokinetic profile and safety profile of the drug substance. Studies showed that doses of 50 to 1600 mg in a micro-emulsion in water were well tolerated. Mild and short-lived side effects were observed including nausea, vomiting, abdominal pain, and mild headaches. These side effects were not dose-related.

Numerous factors will be taken into consideration by a clinician when determining trial doses for testing efficacy of a pharmaceutical composition of the invention comprising a nonimmunosuppressive cyclosporin A derivative of formula I, II or III. Primary among these are the toxicity and half-life of the nonimmunosuppressive cyclosporin A derivative. Additional factors include the size of the patient, the age of the patient, the general condition of the patient (including mechanical ventilation, clinical stage of the disease, the severity of the symptoms), the presence of other drugs in the patient, and the like. A course of treatment will require repeated administration of a pharmaceutical composition of the invention. Typically, an adequate drug dose will be administered about once per day. Because of the genetic nature of the disease, treatment may need to be continued for an extended period of time, possibly for the life of the patient.

No effective pharmacological treatment of UCMD is presently known. Patients are supported by vaccination against influenza and pneumococal infection, and any infection is treated aggressively with antibiotics. Hence, a pharmaceutical composition of the present invention may comprise one or more other active ingredients in addition to a nonimmunosuppressive cyclosporin A derivative such as, for example, one or more antibiotics. The cyclosporin A derivative and such other active ingredient can be administered together as part of the same pharmaceutical composition or can be administered separately as part of an appropriate dose regimen designed to obtain the benefits of all active ingredients. The appropriate dose regimen, the amount of each dose administered, and specific intervals between doses of each active agent will depend upon the specific combination of active agents employed, the condition of the patient being treated, and other factors discussed in the previous section. Such additional active ingredients will generally be administered in amounts equal to those for which they are known to be effective as single therapeutic agents. The FDA approved dosages for such active agents that have received FDA approval for administration to humans are publicly available.

The present invention also relates to the use of a nonimmunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III, for reducing mitochondrial dysfunction and apoptotic rates in cells of patients suffering from BM. Moreover, the invention also concerns a method for treatment of BM in a patient comprising administering to the patient an effective amount of a nonimmunosuppressive cyclosporin A derivative of formula I, more preferably a nonimmunosuppressive cyclosporin A derivative of formula II and most preferably nonimmunosuppressive cyclosporin A derivative [D-MeAla]$^3$-[EtVal]$^4$-CsA of formula III. Further, the invention also relates to use of a nonimmunosuppressive cyclosporin A derivative of formula I, II or III for the manufacture of a medicament intended for the treatment of BM. Finally, the invention relates to pharmaceutical compositions for the treatment of BM comprising an effective amount of a nonimmunosuppressive cyclosporin A derivative of formula I, II or III, a pharmaceutically acceptable carrier and, optionally, an excipient and a diluent.

All patents, patent applications and publications cited herein shall be considered to have been incorporated by reference in their entirety.

The invention is further elaborated by the following examples. The examples are provided for purposes of illustration to a person skilled in the art, and are not intended to be limiting the scope of the invention as described in the claims. Thus, the invention should not be construed as being limited to the examples provided, but should be construed to encompass any and all variations that become evident as a result of the teaching provided herein.

EXAMPLES

Example 1

Figure 1:
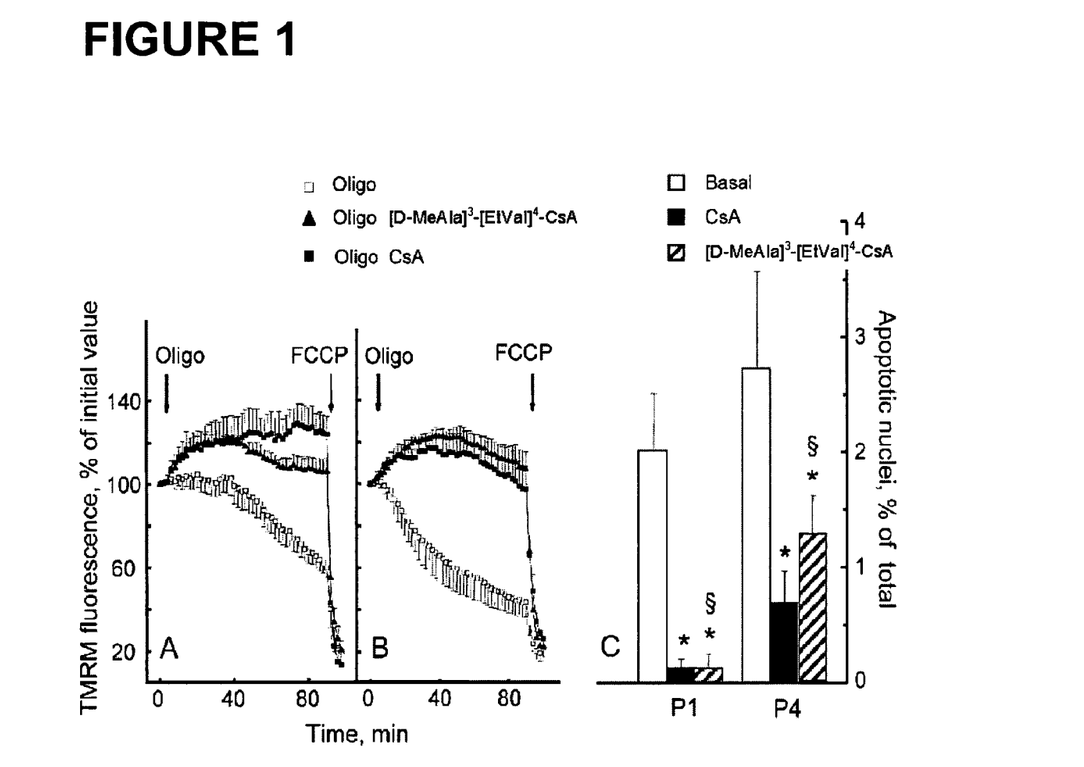
FIG. 1 shows in panels A and B mitochondrial membrane potentials of myoblasts obtained from muscle biopsies of UCMD patients that were exposed to oligomycin and in panel C rates of apoptosis of myoblasts from UCMD patients and healthy individuals.

Effects of Cyclosporin a and Nonimmunosuppressive Cyclosporin A Derivative [D-MeAla]$^3$-[EtVal]$^4$-CsA on Mitochondrial TMRM Fluorescence (Measure of Mitochondrial Membrane Potential) and Incidence of Apoptosis in Myoblast Cultures from UCMD Patients Panels A and B of FIG. 1 show mitochondrial membrane potentials in myoblasts from UCMD patients 1 (A) and 4 (B) as a function of time. Mitochondrial membrane potential was measured based on accumulation of tetramethylrhodamine methyl ester (TMRM). Myoblasts were seeded onto 24 mm round glass coverslips and grown for two days in DMEM supplemented with 20% FCS. The extent of cell and, consequently, mitochondrial loading with potentiometric probes is affected by the activity of the plasma membrane multidrug resistance pump which is inhibited by cyclosporin A. Treatment with cyclosporins may therefore cause an increased mitochondrial fluorescence that can be erroneously interpreted as an increase of mitochondrial membrane potential. To prevent such an artifact and normalize loading conditions, experiments were carried out in the presence of 1.6 µM cyclosporin H, which inhibits the multidrug resistance pump but does not affect PTP. For mitochondrial membrane potential measurements, cells were rinsed once and then incubated in serum-free DMEM supplemented with 1.6 µM cyclosporin H and loaded with 10 nM TMRM for 30 min. At the end of each experiment, mitochondria were fully depolarized by the addition of 4 µM protonophore carbonylcyanide-p-trifluoromethoxyphenyl hydrazone (FCCP). Cellular fluorescence images were acquired with an Olympus IX71/IX51 inverted microscope equipped with a xenon light source (75 W) for epifluorescence illumination and a 12-bit digital cooled CCD camera (Micromax, Princeton Instruments). For detection of fluorescence, 568 +/−25 nm bandpass excitation and 585 nm longpass emission filter settings were used. Images were collected with exposure time of 100 msec using a 40×, 1.3 NA oil immersion objective (Nikon). Data were acquired and analyzed using Cell R software (Olympus). Clusters of several mitochondria (10-30) were identified as regions of interest, and fields not containing cells were taken as the background. Sequential digital images were acquired every 2 min and the average fluorescence intensity was recorded and stored for subsequent analysis. In the experiments shown in panels A and B, cells on glass were loaded with TMRM as discussed, and when indicated by arrows, 6 µM oligomycin (oligo) and 4 µM FCCP were added in the absence of further treatments (open symbols) or after treatment for 30 min with 1.6 µM cyclosporin A (closed squares) or 1.6 µM [D-MeAla]$^3$-[EtVal]$^4$-CsA (closed triangles). Panel C of FIG. 1: Myoblasts from patients 1 (P1) and 4 (P4) were cultured on plastic dishes and scored for the presence of TUNEL-positive nuclei either in the absence of further treatments (basal) or after incubation for 2 hours with 1.6 µM cyclosporin A or 1.6 µM [D-MeAla]$^3$-[EtVal]$^4$-CsA. Data are the mean of at least four independent experiments ±S.D. (*), P<0.01 compared to basal condition. Apoptosis was assessed as described before.

The results reported in FIG. 1 demonstrate that non-immunosuppressive cyclosporin A derivative [D-MeAla]$^3$-[EtVal]$^4$-CsA was as effective as cyclosporin A in preventing oligomycin-dependent mitochondrial depolarization in cells from UCMD patients and restoring the occurrence of apoptosis to the level displayed by cells from healthy donors.

Example 2

Synthesis of [D-MeAla]$^3$-[EtVal]$^4$-CsA (Translated from a Ph.D. thesis by Jean Francois Guichou entitled "De nouveaux analogues de Cyclosporin A comme agent anti-VIH-1", Faculte des Sciences, University of Lausanne, CH-1015 Lausanne, Switzerland (2001)).

Example A

Synthesis of H-MeLeu-Val-MeLeu-Ala-D-Ala-Me-Leu-MeLeu-MeVal-MeBmt(Oac)-Abu-Sar-OMe 4-Dimethylaminopyridine (DMAP) (41.5 mmoles; 5.8 g) was added to a solution of cyclosporin A (CsA) (8.3 mmoles; 10 g) in 100 ml acetic anhydride. The solution was stirred for 18 h at room temperature. The reaction mixture was then diluted with 600 ml ethyl acetate, and washed twice with water and four times with a saturated aqueous solution of sodium bicarbonate. The organic phase was dried over anhydrous $Na_2SO_4$, filtered and solvent was evaporated under reduced pressure. The yellow residue obtained was chromatographed on silica gel (eluent: 98:2 dichloromethane/methanol) and recrystallized in ether. 9.5 g of MeBmt(OAc)-CsA, a white powder, were recovered, representing a yield of 92%.

Trimethyloxonium tetrafluoroborate (22.5 mmoles; 3.3 g) was added to a solution of MeBmt(OAc)—Cs (7.5 mmoles; 9.4 g) in 60 ml dichloromethane. After 16 h at room temperature, 35 ml of 0.26 M sodium methanolate in methanol were added. After 1 h, 35 ml of methanol and 35 ml of 2 N sulphuric acid were added, and the reaction mixture was stirred for another 15 min, neutralized to pH 6.0 with saturated $KHCO_3$ (28 ml) and extracted twice with ethyl acetate. The organic phase was washed 2 times with saturated NaCl, dried over anhydrous $Na_2SO_4$ and filtered. Subsequently, solvent was evaporated under reduced pressure. The residue was chromatographed on silica gel (eluent: 5:1 ethylacetate/methanol). 7.3 g of H-MeLeu-Val-MeLeu-Ala-D-Ala-MeLeu-Me-Leu-MeVal-MeBmt(OAc)-Abu-Sar-OMe were obtained (yield: 76%).

HPLC tr=268.23 nm (98%)

ES/MS: m/z: 1277.5 [M+H$^+$], 639.2 [M+2H$^+$]

Example B

Synthesis of H-Val-MeLeu-Ala-D-Ala-MeLeu-Me-Leu-MeVal-MeBmt(OAc)-Abu-Sar-OMe

DMAP (2.3 mmoles; 334 mg) and phenylisothiocyanate (6.9 mmoles; 0.75 ml) were added to a solution of H-MeLeu-Val-MeLeu-Ala-D-Ala-MeLeu-MeLeu-MeVal-MeBmt (OAc)-Abu-Sar-OMe (4.6 mmoles; 7 g) in 48 ml tetrahydrofuran. After 2 h, solvent was evaporated, and the crude product was chromatographed on silica gel (eluants: 9:1 tert-butyl methyl ether (MTBE)/ethylacetate (1); 9:1 MTBE/methanol (2)). 5.8 g of Ph-NH—C(S)— MeLeu-Val-MeLeu-Ala-D-Ala-MeLeu-MeLeu-MeVal-MeBmt(OAc)-Abu-Sar-OMe were obtained (90% yield).

13.8 ml trifluororacetic acid were added to a solution of the latter compound (4 mmoles; 5.6 g) in 290 ml dichloromethane. After 1 h of reaction, the mixture was neutralized using KHCO$_3$ and diluted with 500 ml dichloromethane. The organic phase was washed 2 times with saturated NaCl, dried over anhydrous Na$_2$SO$_4$ and filtered. Subsequently, solvent was evaporated under reduced pressure. The residue was chromatographed on silica gel (eluants: 9:1 MTBE/ethylacetate (1); 3:1 MTBE/methanol (2)). 2.8 g H-Val-MeLeu-Ala-D-Ala-MeLeu-MeLeu-MeVal-MeBmt(OAc)-Abu-Sar-OMe were obtained (61% yield).

HPLC tr=25.80 nm (99%)
ES/MS: m/z: 1050.5 [M+H$^+$], 547.7 [M+2H$^+$]

Example C

Synthesis of Boc-D-MeAla-EtVal-Val-MeLeu-Ala-D-Ala-MeLeu-MeLeu-MeVal-MeBmt(OAc)-Abu-NMe-CH$_2$—CH$_2$—OH Fluoro-N,N,N',-tetramethylformamidinium hexafluorophosphate (TFFH) (0.96 mmoles; 0.25 g) was added, under an inert atmosphere, to a solution of H-Val-MeLeu-Ala-D-Ala-MeLeu-MeLeu-MeVal-MeBmt(OAc)-Abu-Sar-OMe (0.87 mmoles; 1.00 g), DIPEA (2.78 mmoles; 0.48 ml) and Boc-D-MeAla-EtVal-OH (0.96 mmoles; 0.32 g) in 15 ml dichloromethane. After 15 min, dichloromethane was evaporated, and the residue was taken up in ethylacetate. The organic phase was washed successively with a saturated NaHCO$_3$ solution, a 10% solution of citric acid and a saturated NaCl solution, and was then dried over anhydrous Na$_2$SO$_4$ and concentrated. Chromatography on silica gel (in 98:2 ethylacetate/methanol) yielded 1.14 g (90%) Boc-D-MeAla-EtVal-Val-MeLeu-Ala-D-Ala-MeLeu-MeLeu-MeVal-MeBmt(OAc)-Abu-Sar-OMe.

The latter product (0.64 mmoles; 0.93 g) was taken up in 45 ml anhydrous methanol, and sodium borohydride (25.5 mmoles; 0.96 g) was added in small portions at 15-min intervals over a period of 3 h 30 min. At 4 h, the reaction mixture was cooled to 0° C., hydrolysed by addition of 10% citric acid and concentrated. Residue was taken up in ethylacetate. The organic phase was washed with a 10% solution of citric acid and a saturated NaCl solution, and was then dried over anhydrous Na$_2$SO$_4$ and concentrated. After chromatography on silica gel (in 95:5 ethylacetate/methanol) 0.63 g (81%) of Boc-D-MeAla-EtVal-Val-MeLeu-Ala-D-Ala-MeLeu-MeLeu-MeVal-MeBmt(OAc)-Abu-NMe-CH$_2$—CH$_2$—OH were obtained.

ES/MS: m/z: 1434.9 [M+H$^+$], 717.9 [M+2H$^+$]

Example D

Synthesis of H-D-MeAla-EtVal-Val-MeLeu-Ala-D-Ala-MeLeu-MeLeu-MeVal-MeBmt-Abu-OH

Methanesulfonic acid (3.18 mmoles; 2.060 ml) was added to a solution of Boc-D-MeAla-EtVal-Val-MeLeu-Ala-D-Ala-MeLeu-MeLeu-MeVal-MeBmt(OAc)-Abu-NMe-CH$_2$—CH$_2$—OH (0.425 mmoles; 610 mg) in 42.5 ml methanol, and the mixture was heated to and maintained at 50° C. Progress of the reaction was monitored by HPLC and mass spectrometry. After 80 h, the mixture was cooled to 0° C., and hydrolysed by addition of 1 M NaHCO$_3$. Methanol was eliminated, and the residue was taken up in ethylacetate. The organic phase was washed with 1 M NaHCO$_3$ and then a saturated NaCl solution, dried over anhydrous Na$_2$SO$_4$ and concentrated. The product (557 mg), H-D-MeAla-EtVal-Val-MeLeu-Ala-D-Ala-MeLeu-MeLeu-MeVal-MeBmt(OAc)-Abu-O—CH$_2$—CH$_2$—NHMe, was used in the next step without purification.

Product (0.42 mmoles; 557 mg) was dissolved in 20 ml methanol and combined, under an inert atmosphere, with a solution of sodium methanolate (1.26 mmoles) in 1.26 ml methanol. After 18 h at room temperature, the reaction mixture was cooled to 0° C., and sodium hydroxide (4.2 mmoles; 168 mg) in 5 ml water was added dropwise. After 21 h at room temperature, the reaction mixture was again cooled to 0° C. and neutralized with 1 M KHSO$_4$. Methanol was eliminated, and the residue was dissolved in ethylacetate. The organic phase was washed with a semi-saturated NaCl solution, dried over anhydrous Na$_2$SO$_4$ and concentrated. The product (335 mg; 64%), H-D-MeAla-EtVal-Val-MeLeu-Ala-D-Ala-MeLeu-MeLeu-MeVal-MeBmt-Abu-OH, was used in the next step without purification.

HPLC tr=26.27 nm (86%)
ES/MS: m/z: 1235.5 [M+H$^+$], 618.2 [M+2H$^+$]

Example E

Synthesis of [D-MeAla]$^3$-[EtVal]$^4$-CsA

Under an inert atmosphere, a solution of H-D-MeAla-EtVal-Val-MeLeu-Ala-D-Ala-MeLeu-MeLeu-MeVal-MeBmt-Abu-OH (0.162 mmoles; 200 mg) and sym.collidine (1.78 mmoles; 0.24 ml) in 50 ml dichloromethane was added dropwise to a solution of (7-azabenzotriazole-1-yloxy)tripyrrolidinophosphonium hexafluoro-phosphate (PyAOP, 0.486 mmoles; 254 mg) in 3.2 liter dichloromethane. 72 h later, the reaction mixture was hydrolyzed by addition of a 10% Na$_2$CO$_3$ solution. Dichloromethane was evaporated, and residue taken up in ethylacetate. The organic phase was washed successively with a 0.1 N HCl solution and a saturated solution of NaCl, dried over anhydrous Na$_2$SO$_4$ and concentrated. Crude product was purified on silica gel, yielding 110 mg (59%) [D-MeAla]$^3$-[EtVal]$^4$-CsA HPLC tr=30.54 nm (100%)
ES/MS: m/z: 1217.6 [M+H$^+$], 609.3 [M+2H$^+$]

Example 3

Oral formulations of [D-MeAla]$^3$-[EtVal]$^4$-CsA

Amounts are expressed as % w/w.

Example A

| | |
|---|---|
| [D-MeAla]$^3$-[EtVal]$^4$-CsA | 10 |
| Glycofurol 75 | 35.95 |
| Miglycol 812 | 18 |
| Cremophor RH40 | 35.95 |
| Alpha-Tocopherol | 0.1 |

Example B

| | |
|---|---|
| [D-MeAla]$^3$-[EtVal]$^4$-CsA | 10 |
| Tetraglycol | 2 |
| Captex 800 | 2 |
| Nikkol HCO-40 | 85.9 |
| Butylhydroxytoluene (BHT) | 0.1 |

Example C

| | |
|---|---|
| [D-MeAla]$^3$-[EtVal]$^4$-CsA | 10 |
| Glycofurol 75 | 39.95 |
| Miglycol 812 | 14 |
| Cremophor RH40 | 36 |
| Butylhydroxyanisole (BHA) | 0.05-0.1 |

Example D

| | |
|---|---|
| [D-MeAla]$^3$-[EtVal]$^4$-CsA | 10 |
| Tetraglycol | 10 |
| Myritol | 5 |
| Cremophor RH40 | 74.9 |
| Alpha-Tocopherol | 0.1 |

Example E

| | |
|---|---|
| [D-MeAla]$^3$-[EtVal]$^4$-CsA | 10 |
| Ethanol | 9 |
| Propylene glycol | 8 |
| Cremophor RH40 | 41 |
| Glycerol monolinoleate | 32 |

For individual components of formulations A-D and for methods of preparation see British Patent Appl. No. 2,222,770.

Example 4

Therapeutic Efficacy of [D-MeAla]$^3$-[EtVal]$^4$-CsA in Collagen VI Knockout Mice One group of four collagen VI knockout mice (Col6a1$^{-/-}$; 5-6 months of age; gender-balanced) was administered i.p. twice daily for 5 days a dose of 5 mg/kg of [D-MeAla]$^3$-[EtVal]$^4$-CsA. A control group of four animals was subjected to a similar regimen of a placebo formulation. Following sacrifice, a blood sample was collected from each animal, then the liver and the muscles from the hind legs were isolated and processed for preparing mitochondria for calcium retention capacity (CRC) assays. At the same time, the diaphragm and flexor digitorum brevis (FDB) muscles were isolated and processed for histopathology and in situ mitochondrial function assessment (mitochondrial transmembrane potential). All in vivo experiments were approved by the appropriate agencies and were performed according to agency guidelines.

Methods

Preparation of Mitochondria and CRC Assays

Mitchondria were prepared from liver and muscle homogenates by differential centrifugation as described in Fontaine et al. 1998. J. Biol. Chem. 273: 25734-25740 and Fontaine and Bernardi. 1999. J. Bioenerg. Biomembr. 31: 335-345. CRC of mitochondrial preparations was assessed fluorimetrically in the presence of $Ca^{2+}$ indicator Calcium Green-5N (Molecular Probes; excitation: 505 nm; emission: 535 nm) using a PerkinElmer LS50B spectrofluorimeter equipped with magnetic stirring and thermostatic control. Incubation medium contained 0.25 M sucrose, 10 mM Tris-MOPS, 5 mM glutamate, 2.5 mM malate, 1 (liver) or 10 (muscle) mM Pi-Tris, 20 µM EGTA-Tris and 1 µM Calcium Green-5N (pH 7.4).

Isolation and Culture of Skeletal Myofibers and TMRM Assay

FDB fibers were isolated as described in Irwin et al. 2003. Nat. Genet. 35: 267-271. Intact myofibers were plated on glass coverslips coated with laminin (3 µg/cm$^2$) and cultured in Dulbecco's modified Eagle medium containing 10% fetal calf serum. For the experiment, FDB fibers were placed in 1 ml Tyrode's buffer and loaded with 20 nM TMRM (Molecular Probes) as described in Irwin et al. Images of mitochondrial TMRM fluorescence were acquired using an Olympus IX71/IX51 inverted microscope.

TUNEL assay

After fixation in 4% paraformaldehyde and paraffin embedding, 7 µm sections of muscle diaphragm were prepared. TUNEL was performed using the ApopTag in situ apoptosis detection kit (Intergen). Samples were stained with peroxidase/diaminobenzidine to detect TUNEL-positive nuclei and counterstained with Hoechst 33258 (Sigma) to mark all nuclei as described in Irwin et al. Numbers of total and TUNEL-positive nuclei in randomly selected fibers were determined using a Zeiss Axioplan microscope equipped with a Leica DC 500 camera.

Results

Figure 2:
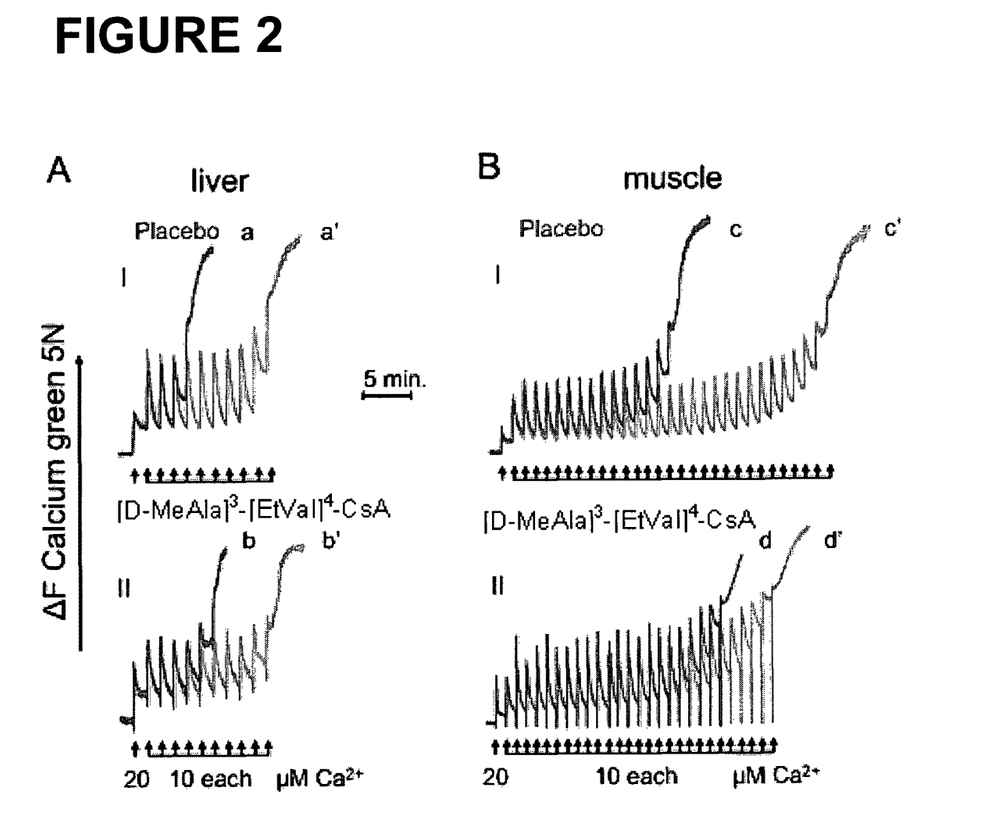
FIG. 2 Representative experiment testing the effect of [D-MeAla]$^3$-[EtVal]$^4$-CsA on the calcium retention capacity (CRC) of liver and muscle mitochondria isolated from Col6a (1)$^{-/-}$ mice. Where indicated by arrows, pulses of 10 μM Ca$^{2+}$ were added. Mitochondria examined in panels AI and BI were isolated, 5 hours after their last treatment, from placebo-treated mice, and those in panels AII and BII from mice treated with [D-MeAla]$^3$-[EtVal]$^4$-CsA. Traces a-d: no addition; traces a'-d': [D-MeAla]$^3$-[EtVal]$^4$-CsA (0.8 μM) was added to the incubation medium. Data are representative of 4 replicate experiments.
Figure 3:
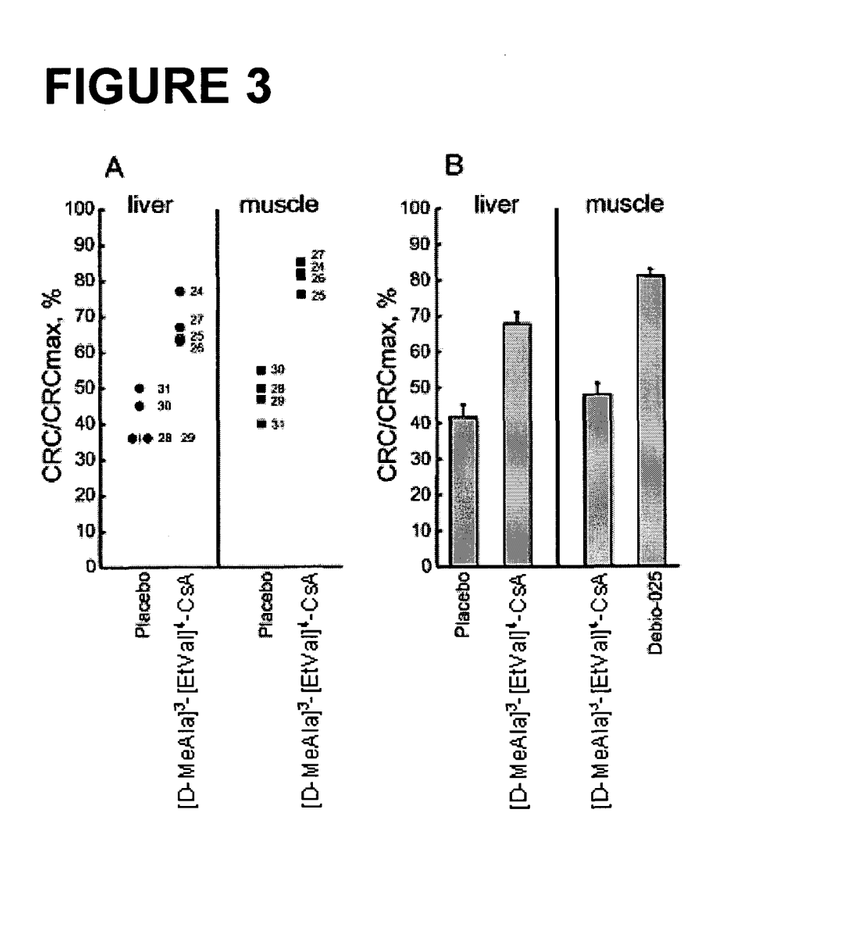
FIG. 3 Summary of CRC determinations on mitochondria isolated from liver and muscle of Col6a1−/− mice after treatment with placebo or [D-MeAla]$^3$-[EtVal]$^4$-CsA. Experiments were carried out as described in FIG. 2. CRCmax refers to the CRC observed after addition of 0.8 μM [D-MeAla]$^3$-

Effect of [D-MeAla]$^3$-[EtVal]$^4$-CsA on the Permeability Transition Pore (PTP) Ex Vivo Energized mitochondria from liver and hindleg muscles isolated from Col6a1$^{-/-}$ mice after treatment with [D-MeAla]$^3$-[EtVal]$^4$-CsA or a placebo formulation were incubated in the presence of Calcium Green-5N which monitors extramitochondrial $Ca^{2+}$. A train of $Ca^{2+}$ pulses was then administered, each pulse being taken up until a threshold concentration was reached that caused opening of the PTP. This protocol allowed for a detailed analysis of effects of both PTP sensitizers and desensitizers. (Fontaine et al. 1998.) Results showed a significant desensitization of the PTP to $Ca^{2+}$ and Pi in both liver and muscle mitochondria from mice treated with [D-MeAla]$^3$-[EtVal]$^4$-CsA, as shown by an increased $Ca^{2+}$ threshold for PTP opening (FIG. 2). This effect was particularly striking for muscle mitochondria, the CRC reaching close to the maximum level attainable by direct addition of [D-MeAla]$^3$-[EtVal]$^4$-CsA to the incubation medium. See panel BII, trace d vs. trace d'. A summary of results obtained from analyses of mitochondria from four [D-MeAla]$^3$-[EtVal]$^4$-CsA-treated (mice #24-27) and four placebo-treated mice (mice #28-31) is shown in FIG. 3.

Figure 4:
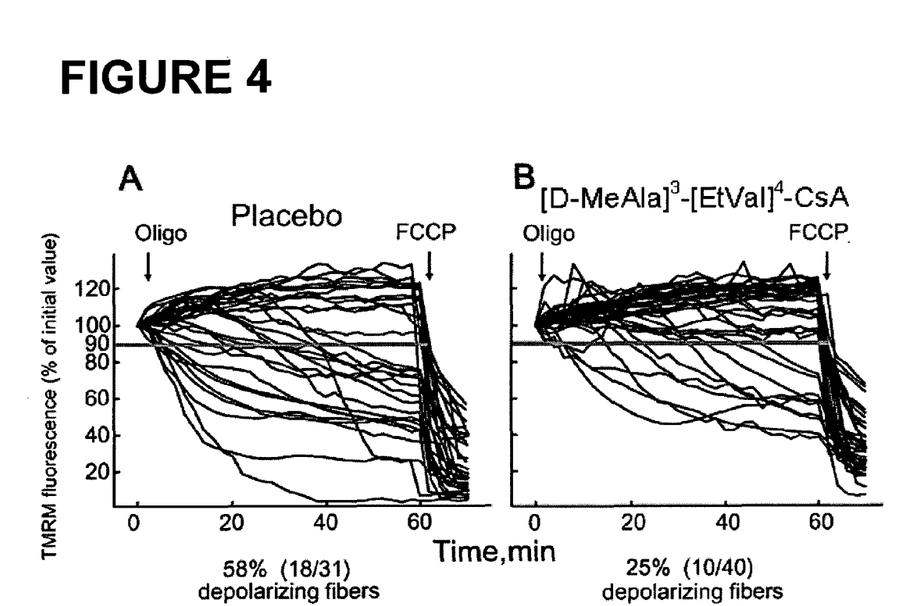
FIG. 4 Effect on mitochondrial TMRM fluorescence of oligomycin in FDB fibers isolated from Col6a1−/− mice treated with placebo or [D-MeAla]$^3$-[EtVal]$^4$-CsA. TMRM assays were performed as described under Example 4 (Methods). Where indicated, 5 μM oligomycin (Oligo) or 4 μM carbonylcyanide-p-trifluoromethoxyphenyl hydrazone (FCCP) were added. Each trace represents the fluorescence values for a single fiber. The figure also displays the number of fibers depolarizing after oligomycin addition relative to a threshold value set arbitrarily at 90% fluorescence.

Effect of [D-MeAla]$^3$-[EtVal]$^4$-CsA on the Mitochondrial Transmembrane Potential in FDB Fibers Mitochondrial transmembrane potential was assessed by mitochondrial fluorescence changes of tetramethylrhodamine methylester (TMRM), a fluorescence probe that accumulates in polarized mitochondria and is released when the transmembrane potential decreases. it was previously shown that a mitochondrial dysfunction in Col6a1$^{-/-}$ muscle fibers is unmasked by oligomycin, which is an inhibitor of mitochondrial F1F0-ATP synthase. Addition of oligomycin to fibers isolated from placebo-treated Col6a1$^{-/-}$ mice resulted in the expected decrease in TMRM fluorescence in most of the fibers (FIG. 4A). Treatment in vivo with [D-MeAla]$^3$-[EtVal]$^4$-CsA significantly decreased the number of fibers in which mitochondrial depolarization could be observed (FIG. 4B). Table 1 summarizes the results for each individual mouse treated with placebo or [D-MeAla]$^3$-[EtVal]$^4$-CsA, respectively.

TABLE 1

Fibers depolarizing following oligomycin addition

| Group | Mouse # | Number of fibers depolarizing after oligomycin addition | Total number of fibers |
|---|---|---|---|
| 2 (placebo) | 28 | 3 | 6 |
| | 29 | 6 | 8 |
| | 30 | 4 | 8 |
| | 31 | 5 | 9 |
| 1 ([D-MeAla]$^3$-[EtVal]$^4$-CsA) | 24 | 4 | 12 |
| | 25 | 2 | 8 |
| | 26 | 4 | 10 |
| | 27 | 0 | 10 |

Effect of [D-MeAla]$^3$-[EtVal]$^4$-CsA on Diaphragm Apoptosis

Figure 5:
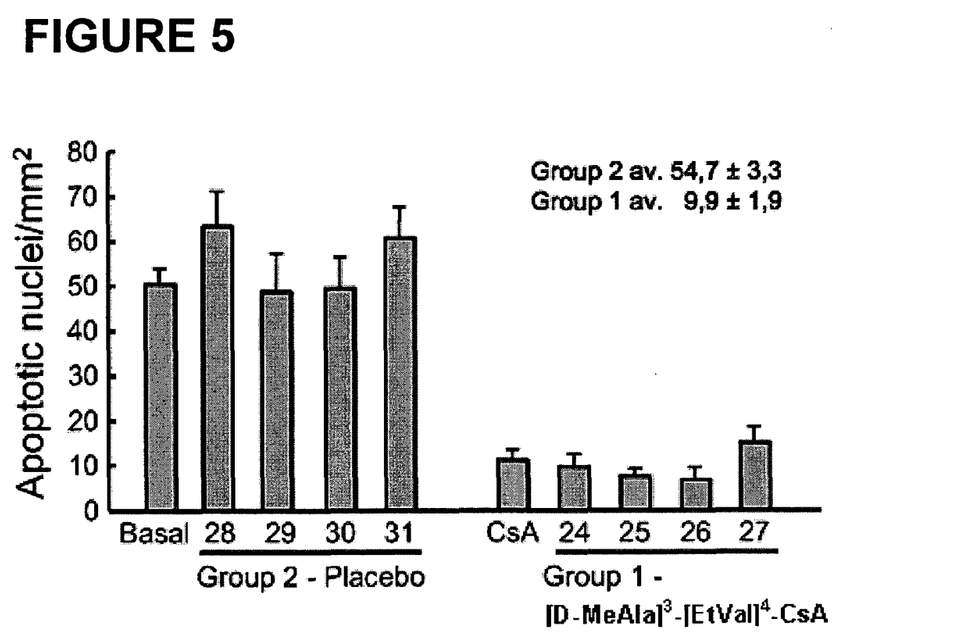
FIG. 5 Incidence of apoptosis in diaphragm sections from Col6a1$^{-/-}$ mice treated with [D-MeAla]$^3$-[EtVal]$^4$-CsA or placebo. Indicated are numbers of apoptotic nuclei per mm$^2$ in the diaphragm sections from each Col6a1$^{-/-}$ mouse treated with [D-MeAla]$^3$-[EtVal]$^4$-CsA (group 1, mice #24-27) or placebo (group 2, mice #28-31). Bars refer to averages of 20-30 sections per mouse +/−SD. Data for untreated (basal) and CsA (cyclosporin A)-treated animals are from historical samples.

The diaphragm from each of the [D-MeAla]$^3$-[EtVal]$^4$-CsA-(#24-27) or placebo-treated (#28-31) Col6a1$^{-/-}$ mice was sectioned. Twenty to thirty sections per animal were examined by TUNEL assay. Diaphragm fibers from mice treated with [D-MeAla]$^3$-[EtVal]$^4$-CsA showed a dramatic decrease of apoptotic nuclei compared to those treated with placebo (FIG. 5). The in vivo treatment with [D-MeAla]$^3$-[EtVal]$^4$-CsA was as effective as that with CsA.

Ultrastructural Evaluation

Figure 6:
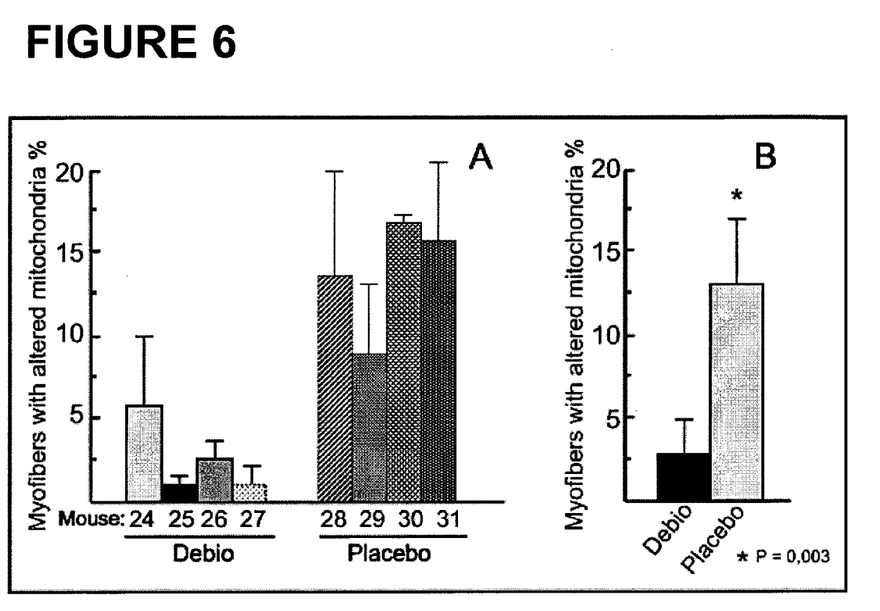
FIG. 6 Assessment of fibers with altered mitochondria in diaphragm from Col6a1$^{-/-}$ mice treated with [D-MeAla]$^3$-[EtVal]$^4$-CsA or placebo. Panel A shows percentages of muscle fibers with altered mitochondria detected by electron microscopy in samples from individual animals. Panel B shows mean values for the two treatment groups. Bars refer to average percentages +/−SD. Significance was calculated using the Mann-Whitney test.

Samples of diaphragm muscles from [D-MeAla]$^3$-[EtVal]$^4$-CsA-(#24-27) or placebo-treated (#28-31) Col6a1$^{-/-}$ mice were gently stretched on a dental wax support to prevent contraction during fixation. For fixation, the samples were incubated in 0.1 M phosphate buffer (pH 7.4) containing 2.5% glutaraldehyde for 3 hours at 4° C., washed overnight in 0.15 M phosphate buffer, post-fixed in 1% osmium tetroxide in veronal, dehydrated and embedded in Epon 812 epoxy resin. Ultrathin section were stained with uranyl acetate and lead citrate and observed in a Philips EM 400 transmission electron microscope operating at 100 kilovolts. For statistical analysis, 300 muscle fibers from three different blocks of each sample tissue were studied (FIG. 6). A significantly decreased number of fibers with altered mitochondria showing a swollen appearance or exhibiting electrodense inclusions was counted in [D-MeAla]$^3$-[EtVal]$^4$-CsA-treated mice (#24-27) when compared to the control mice (#28-31).

Analogous experiments were carried out on Col6a1$^{-/-}$ mice treated p.o. (per orally) with a formulation comprising [D-MeAla]$^3$-[EtVal]$^4$-CsA or a placebo formulation. Clear increases in CRC in muscle mitochondria from [D-MeAla]$^3$-[EtVal]$^4$-CsA-treated animals were observed, indicating PTP desensitization by the cyclosporin. Furthermore, TUNEL assays on diaphragm sections indicated that in vivo treatment with [D-MeAla]$^3$-[EtVal]$^4$-CsA resulted in a dramatically reduced incidence of apoptosis.

Example 5

Preliminary Clinical Trial of [D-MeAla]$^3$-[EtVal]$^4$-CsA on UCMD and BM Patients Five patients were enrolled, of which four suffered from UCMD and one of BM. The patients had mutation in their COL6A1, COL6A2 or COL6A3 genes, respectively. The trial was designed to test whether treatment with CsA was effective in reducing mitochondrial dysfunction as assessed by the ability of oligomycin to cause mitochondrial depolarization in muscle fibers. Depolarization was detected as a change in TMRM fluorescence. Patients were treated with a daily oral dose of 5 mg/kg CsA for a period of thirty days. Muscle biopsies were taken immediately before and after the treatment period and were processed for TMRM assay. Results averaged over the five patients revealed that oligomycin induced 90% of muscle cells to depolarize prior to treatment, but only 37% subsequent to treatment. Thus, short-term treatment with CsA was capable of substantially reducing mitochondrial dysfunction as assayed by oligomycin-induced depolarization.

The invention claimed is:

1. A method for treatment of Ullrich congenital muscular dystrophy or Bethlem myopathy in a patient comprising administering to the patient an effective amount of a nonimmunosuppressive cyclosporin A derivative of formula I wherein
W is MeBmt, dihydro-MeBmt, 8'-hydroxy-MeBmt or O-actetyl-MeBmt,
X is αAbu, Val, Thr, Nva or O-methyl threonine (MeOThr),
R is Pro, Sar, (D)-MeSer, (D)-MeAla, or (D)-MeSer(Oacetyl),
Y is MeLeu, thioMeLeu, v-hydroxy-MeLeu, MeIle, MeVal, MeThr, MeAla, MeaIle or MeaThr; N-ethyl Val (EtVal), N-ethylIle, N-ethylThr, N-ethylPhe, N-ethylTyr or N-ethylThr(Oacetyl), wherein Y cannot be MeLeu when R is Sar,
Z is Val, Leu, MeVal or MeLeu,
Q is MeLeu, v-hydroxy-MeLeu, MeAla or Pro,
T$_1$ is (D)Ala or Lys,
T$_2$ is MeLeu or γ-hydroxy-MeLeu, and
T$_3$ is MeLeu or MeAla.

2. The method of claim 1, wherein the nonimmunosuppressive cyclosporin A derivative is a cyclosporin derivative of formula II wherein
W' is MeBmt, dihydro-MeBmt, or 8'-hydroxy-MeBmt,
X is αAbu, Val, Thr, Nva or O-methyl threonine (MeOThr),
R' is Sar, (D)-MeSer, (D)-MeAla, or (D)-MeSer(Oacetyl),
Y' is MeLeu, v-hydroxy-MeLeu, MeIle, MeVal, MeThr, MeAla, MeaIle or MeaThr;
N-ethylVal (EtVal), N-ethylIle, N-ethylThr, N-ethylPhe, N-ethylTyr or N-ethylThr(Oacetyl), wherein Y cannot be MeLeu when R is Sar,
Z is Val, Leu, MeVal or MeLeu,
Q' is MeLeu, v-hydroxy-MeLeu, or MeAla.

3. The method of claim 1, wherein the non-immunosuppressive cyclosporin A derivative is the nonimmunosuppressive cyclosporine [D-MeAla]$^3$-[EtVal]$^4$-CsA of formula III

| ─MeBmt-αAbu-D-MeAla-EtVal-Val-MeLeu-Ala-(D)Ala-MeLeu-MeLeu-MeVal─ |
|:---:|
| 1  2  3  4  5  6  7  8  9  10  11 | wherein MeBmt is N-methyl-(4R)-4-but-2E-en-1-yl-4-methyl-(L)threonine, αAbu is L-α-aminobutyric acid, D-MeAla is N-methyl-D-alanine, EtVal is N-ethyl-L-valine, Val is L-valine, MeLeu is N-methyl-L-leucine, Ala is L-alanine, (D)Ala is D-alanine, and MeVal is N-methyl-L-valine.

* * * * *